Figure 1:
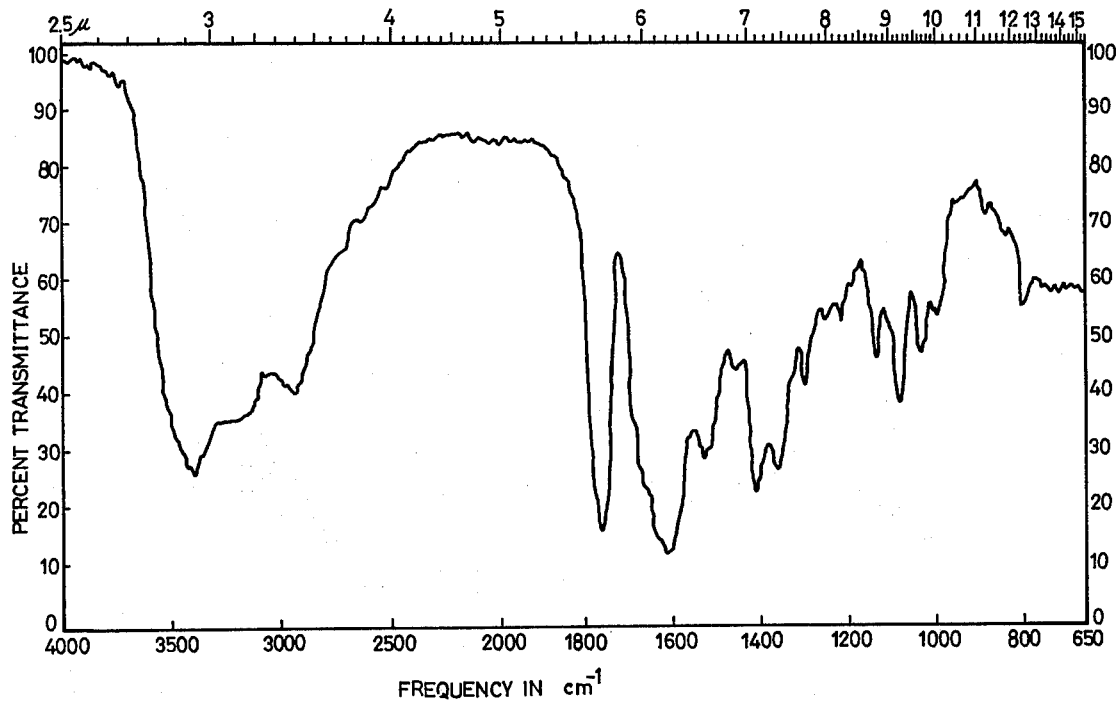

United States Patent [19]

Shomura et al.

[11] 3,974,035
[45] Aug. 10, 1976

[54] PROCESS FOR PREPARING A CEPHAMYCIN TYPE ANTIBIOTIC SUBSTANCE

[75] Inventors: Takashi Shomura; Hiroshi Watanabe; Yasuaki Ogawa; Kazunori Ohba; Yasumitsu Kondo, all of Yokohama; Michio Kojima, Tokyo; Shigeharu Inoje; Taro Niida, both of Yokohama, all of Japan

[73] Assignee: Meiji Seika Kaisha, Ltd., Tokyo, Japan

[22] Filed: Feb. 24, 1975

[21] Appl. No.: 552,281

[30] Foreign Application Priority Data
Mar. 6, 1974 Japan............................. 49-25107

[52] U.S. Cl............................. 195/36 C; 195/80 R
[51] Int. Cl.².......................................... C12D 9/14

[58] Field of Search...................... 195/80 R, 36 C

[56] References Cited
UNITED STATES PATENTS

| 3,770,590 | 11/1973 | Inamine et al. | 195/36 C |
| 3,862,008 | 1/1975 | Hamill et al. | 195/80 R |
| 3,865,693 | 2/1975 | Arai et al. | 195/80 R |

Primary Examiner—Alvin E. Tanenholtz
Attorney, Agent, or Firm—Flynn & Frishauf

[57] ABSTRACT

This invention relates to a process for preparing a cephamycin type antibiotic substance which comprises cultivating a microorganism belonging to the genus Streptomyces under aerobic conditions and a primary object of this invention is to provide a process for preparing the said product on a simple and industrial scale.

6 Claims, 2 Drawing Figures

PROCESS FOR PREPARING A CEPHAMYCIN TYPE ANTIBIOTIC SUBSTANCE

This invention relates to a new product and a process for the fermentative production of 7-(5-amino-5-carboxyvaleramido)-7-methoxy-3-hydroxymethyl-3-cephem-4-carboxylic acid which is a cephalosporin-type antibiotic substance. More particularly, this invention relates to a process for the production of 7-(5-amino-5-carboxyvaleramido)-7-methoxy-3-hydroxymethyl-3-cephem-4-carboxylic acid which comprises cultivating a microorganism belonging to the genus Streptomyces capable of producing 7-(5-amino-5-carboxyvaleramido)-7-methoxy-3-hydroxymethyl-3-cephem-4-carboxylic acid under aerobic conditions to accumulate said substance and recovering said substance.

The desired product of the present process, 7-(5-amino-5-carboxyvaleramido) -7-methoxy-3-hydroxymethyl-3-cephem-4-carboxylic acid, is represented by the following formula

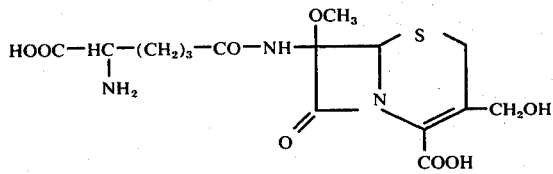

and it is not only an antibacterial substance but also has properties suggesting that the substance may a promising starting material for the synthesis of various cephalosporintype derivatives.

It is disclosed that 7-(5-amino-5-carboxyvaleramido)-7-methoxy-3-hydroxymethyl-3-cephem-4-carboxylic acid is obtainable from cephamycin C through a chemical reaction with five stages (Japanese Patent Provisional Publication No. 3286/1971), but its physico-chemical properties and biological activities are not disclosed therein.

As a result of our research for a new process for the production of said substance, it has been detected that the substance is obtained by cultivation of a strain of actinomycetes. The substance is isolated from the culture broth and identified as 7-(5-amino-5-carboxyvaleramido)-7-methoxy-3-hydroxymethyl-3-cephem-4-carboxylic acid by measurement of its physico-chemical and biological properties.

More specifically, it has been found that a new strain, Streptomyces chartreusis strain SF-1623 (Deposit number 2348 in Fermentation Research Institute of Agency of Industrial Science and Technology, Chiba, Japan and ATCC number 21999 in American Type Culture Collection in Washington D.C., U.S.A.), which is used for the production of the new antibiotic substance SF-1623 isolated previously by this inventors (Japanese Patent Application No. 132594/1973) produces 7-(5-amino-5-carboxyvaleramido) -7-methoxy-3-hydroxymethyl-3-cephem-4-carboxylic acid, and this invention has been completed upon this finding.

The gist of this invention is, accordingly, a process for the production of 7-(5-amino-5-carboxyvaleramido)-7-methoxy-3-hydroxymethyl-3-cephem-4-carboxylic acid which comprises cultivating a microorganism belonging to the genus Streptomyces capable of producing 7-(5-amino-5-carboxyvaleramido)-7-methoxy-3-hydroxymethyl-3-cephem-4-carboxylic acid under aerobic conditions to accumulate said substance in the culture broth and recovering said substance therefrom. An example of the microorganism which is used in the process of this invention and capable of producing 7-(5-amino-5-carboxyvaleramido)-7-methoxy-3-hydroxymethyl-3-cephem-4-carboxylic acid, is Streptomyces chartreusis strain SF-1623.

This invention provides not only a new and direct method for the production of 7-(5-amino-5-carboxyvaleramido)-7-methoxy-3-hydroxymethyl-3-cephem-4-carboxylic acid, but also the method according to this invention has remarkable advantages as compared with the well-known method for preparing this substance from the fermentation product cephamycin C through five chemical stages, namely the method of Japanese Patent Provisional Publication No. 3286/1971.

Morphological characteristics of the above strain No. SF-1623 are as follows:

I. Morphological properties

Aerial mycelium is abundantly grown on starch agar, yeast-malt-agar and oatmeal-agar, and spore formation is abundant.

The mycelium produces monopodially branches but does not produce whorl. The aerial hyphae are terminated with spirals (predominantly opened spirals). No particular shapes such as sclerotium are observed. The surface structure of the spore is spiny when observed under an electron microscope. The spores are ellipsoidal to spherical in shape and 0.5–0.8 × 0.8–1.0 $\mu$ in size. Mature spore chains with more than 10 spores per the chain are usually produced.

II. Cultural characteristics on various culture media
As shown in the table below:

| Medium | Growth (Reverse) | Aerial mycelium | Soluble pigment |
| --- | --- | --- | --- |
| Sucrose nitrate agar | Faintly yellowish brown to yellowish brown | White to greyish white | Faintly amber (No change upon pH) |
| Glucose asparagine agar | Cream to faintly yellowish brown | Poor, white | None |
| Glycerine asparagine agar | yellowish cream | Poor white | None |
| Starch agar | Good, yellowish brown | Abundant, greyish blue to greenish blue | None |
| Oatmeal agar | Good, yellowish cream | Abundant, blueish grey | None |
| Yeast malt agar | Good, deep brown | Abundant, greyish blue to greenish blue | Brown (No change upon pH) |
| Nutrient agar | Poor, colorless | None | None |
| Tyrosine agar | Good, dark brown to black | Abundant, greyish blue | Brown (No change upon pH) |
| Potato | Swollen to rising, yellowish brown | White | None |

(Note) All cultivation temperatures of 28°C.

III. Physiological properties
1. Temperature range for growth: Grows on yeast-malt agar medium in a temperature range of 10°–42°C. 2. Gelatin liquefaction: Gelatine is slightly liquefied on cultivation at 20°C. for 30 days.

3. Starch hydrolysis: Positive (28°C., highly) 4. Skimmed milk coagulation: Positive (37°C.), negative (28°C.). Skimmed milk peptonization: Positive (37°C., 28°C.)

5. Melamine-like pigment formation: Positive

IV. Carbon source utilization (on Pridham-Gottlieb's agar medium): All carbon sources as listed below are positively utilized.

D-glucose, D-fructose, D-mannitol, D-xylose, L-arabinose, L-inositol, rhamnose, sucrose, raffinose The above-mentioned characteristics of the strain SF-1623 may be summarised as follows; the aerial hyphae are of spiral (opened), and the surface structure of the spore is spiny. The colorings of the reverse side of the growth is cream to yellowish brown to brown without any particular color. The aerial mycelium is greyish blue to greenish blue. Brown melanine-like pigment is produced on organic media. Formation of any other soluble pigment than the melanine-like pigment is scarcely observed, but pale amber (no change upon pH) pigment is produced on sucrose-nitrate medium.

Searching the closely related strains to the strains to the strains SF-1623 by referring to the disclosure of International Streptomyces Project (ISP) in the International Journal of Systematic Bacteriology, Vol. 18, pages 69–189, pages 279–392 (1968), Vol. 19, pages Vol. 22, pages 265–394 (1972) and that by W. H. TREJO & R. E. BENNETT: J. Bacteriol., Vol. 85, pages 676–690 (1963), it has been found that the present strain SF-1623 most closely resembles to *Streptomyces chartreusis*.

More specifically, both strains are completely identical in morphological characteristics; in respect to formation of spirals and spiny spores, formation of arerial mycelium of bluish color and of melanine-like pigment, and they are also well identical in the color of growth and sugar utilization. From comparative studies in details of the both strains. It is found that the strain SF-1623 produces a soluble pigment of pale amber on sucrose-nitrate medium and a soluble pigment of brown color on tyrosine medium, whereas *Streptomyces chartreusis* does not produce any soluble pigments on these media.

From the foregoing, it is reasonable that the strain SF-1623 is to be identified as a strain of *Streptomyces chartreusis* since the strain is well identical with *Streptomyces chartreusis* in basic properties, though some differences are present between both strains. Therefore, we have designated the strain SF-1623 as *Streptomyces chartreusis* SF-1623 to distinguish this strain from well-known strains and deposited the strain in the name of Streptomyces-SP-SF-1623 under (Deposit number 2348 in the Fermentation Research Institute, Chiba, Japan).

As seen in other strains of the genus Streptomyces, the strain SF-1623 is not definite in its properties and may be varied by artificial variation means such as X-ray, ultraviolet ray, high frequency, radioactive ray, chemical et al. and the strains which may be employed in the process of this invention include all of the strains which belong to the genus Streptomyces and are capable of producing 7-(5-amino-5-carboxyvaleramido)-7-methoxy-3-hydroxymethyl-3-cephem-4-carboxylic acid, including even the above variants.

In a practical embodiment of the process of this invention, the production of 7-(5-amino-5-carboxyvaleramido)-7-methoxy-3-hydroxymethyl-3-cephem-4-carboxylic acid is achieved by cultivating *Streptomyces chartreusis* strain SF-1623 in a culture medium. As the method for cultivation of this strains, liquid cultivation is advantageous a liquid culture, in particular, submerged liquid cultivation is most preferable similarly to the general processes for the production of antibiotics. As a culture medium may be utilized any of well-known media generally used for the cultivation of microorganisms belonging to the genus Streptomyces. For instance, as a carbon source may be employed glucose, glycerol, starch, dextrin, sucrose, starch syrup, molasses, soybean oil and the like. As a nitrogen source may be employed soybean meal, wheat embryo, peptone, meat extract, dry yeast, corn steep liquor, fish meal, ammonium sulfate, sodium nitrate and the like. In addition to the above sources, inorganic salts such as calcium carbonate, sodium chloride, potassium chloride, phosphates and so on may be added, if necessary, also other organic and inorganic substances may be optionally added for the growth promotion of a microorganism and for the increased production of 7-(5-amino-5-carboxyvaleramido)-7-methoxy-3-hydroxymethyl-3-cephem-4-carboxylic acid. For example, L-cystein is an effective promoting substance for the increased production of the present antibiotic substance. Cultivation temperature is in accordance with that generally applied for ordinary microorganisms belonging to the genus Streptomyces, but about 22°– about 35°C is preferable. A pH of the medium is suitably within or around neutral range. The optimum cultivation period for the cultivation in this invention is 60–80 hours in the case of submerged cultivation.

For assay of 7-(5-amino-5-carboxyvaleramido)-7-methoxy-3-hydroxymethyl-3-cephem-4-carboxylic acid the following method is employed.

As the medium for assay a medium having a composition of 1.0 % polypeptone, 0.5 % meat extract, 0.5 % sodium chloride, 2.0 % agar (pH 7) is employed. *Vibrio percolans* ATCC 8461 is used for assay and a cup plate method is adopted. Sample is incorporated in a test plate with a standing cup, which is then in a refrigerator at 5°C. for 16 hours. Thereafter, cultivation is effected at 37°C. and the diameter of an inhibition zone is measured. 7-(5-amino-5-carboxyvaleramido)-7-methoxy-3-hydroxymethyl-3-cephem-4-carboxylic acid shows a linear relationship between the logarithm of a concentration and the diameter of an inhibition zone at 100 mcg/ml–800 mcg/ml in the assay and provides inhibition zone of 12.0–24.0 mm, respectively.

By cultivation of the strain SF-1623, 7-(5-amino-5-carboxyvaleramido)-7-methoxy-3-hydroxymethyl-3-cephem-4-carboxylic acid is predominantly produced and accumulated in a cultured broth. The present substance is a water-soluble, acidic one and thus it is convenient for recovery to extract it from the cultured broth, using such adsorbents as an ion exchange resin, active charcoal and so on. For instance, the active ingredient in the cultured broth is adsorbed on an anion exchange resin Dowex 1 × 2 (Cl-form) and then eluted with a suitable salt solution. This procedure is an effective means for extraction of the present substance. The crude product may be further purified by a column chromatography using Sephadex et al. Further, it is possible by a particular selection of the cultivation condition to inhibit substantial production of the substance SF-1623.

The 7-(5-amino-5-carboxyvaleramido)-7-methoxy-3-hydroxymethyl-3-cephem-4-carboxylic acid isolated by the process of this invention is advantageously recovered in the form of not only a free acid but, usually, a salt with an alkali metal, an alkaline earth metal, ammonium, an organic amine and the like. The physico-chemical properties of 7-(5-amino-5-carboxyvaleramido)-7-methoxy-3-hydroxymethyl-3-cephem-4-carboxylic acid (sodium salt) are as shown below.

Figure 2:
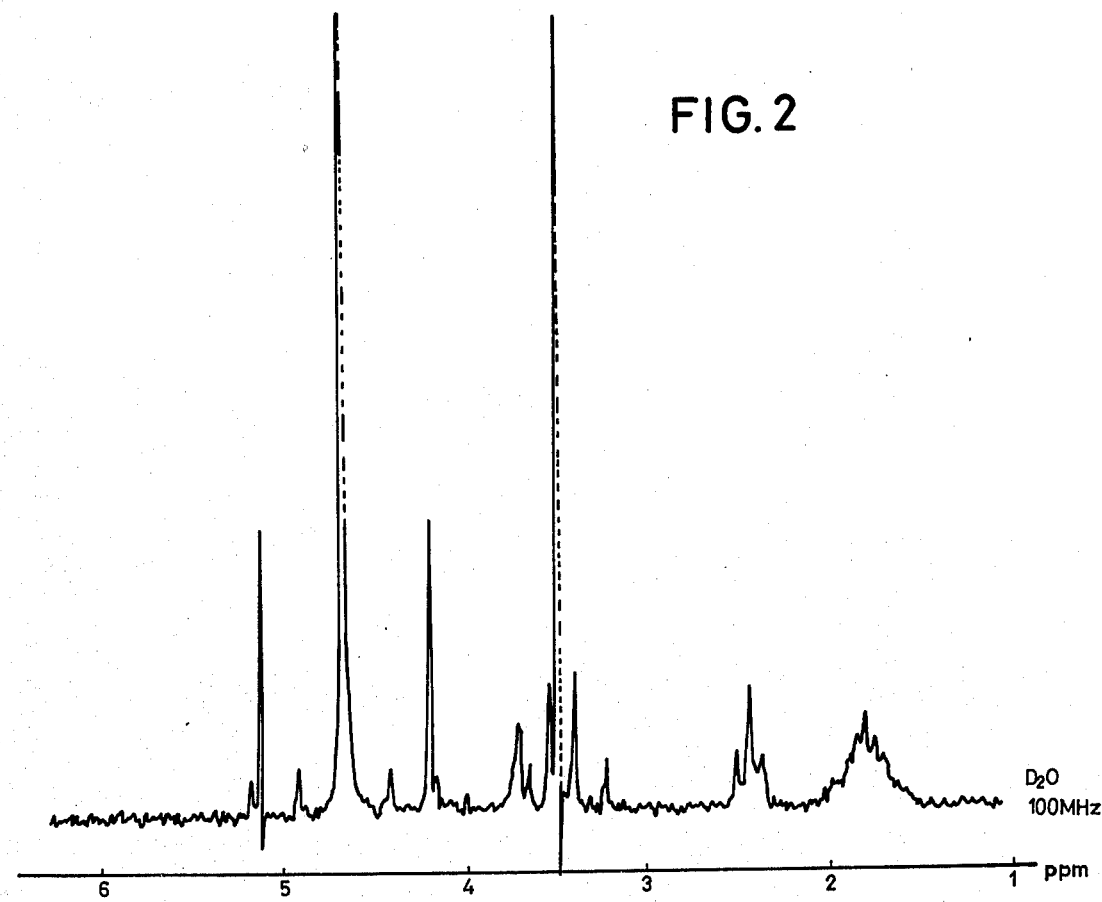

1. Melting point: 165°–172°C. (with decomp.)
2. Specific rotation: $[\alpha]_D^{20} + 168°$ (C/, $H_2O$)
3. Ultraviolet (in aqueous soln.) absorption max.:
   $\lambda_{max}$ 264 m$\mu$, $E_1$ $_{cm}^{1\%}$ = 154
   $\lambda_{max}$ 241 m$\mu$, $E_1$ $_{cm}^{1\%}$ = 124
4. Infrared absorption spectrum: 1763 cm$^{-1}$ ($\beta$-lactam). Infrared absorption spectrum curve in KBr tablet is shown in FIG. 1.
5. Nuclear Magnetic resonance spectrum:
   $\delta$ 4.2 (C-3, $CH_2OH$)
   $\delta$ 3.5 (C-7, $OCH_3$)
   Nuclear Magnetic resonance spectrum in heavy water is shown in FIG. 2.
6. Elementary analysis: Found: C, 43.08; H, 4.98; N, 9.62; S, 7.29. Calculated: C, 42.35; H, 4.71; N, 9.85; S, 7.53 (for $C_{15}H_{20}N_3O_8SNa$).
7. Coloring reaction: Positive in ninhydrin and potassium permanganate
8. Solubility: Soluble in water, sparingly soluble in alcohol, acetone, ethyl acetate, benzene and the like.
9. Rf value in silica gel thin-layer chromatography: 0.31 (n-butanol: acetic acid: water = 2:1:1).

The antibacterial activity of the present substance (in the form of its sodium salt) is as shown below.

produced in a cultured broth under the above cultivation condition. The resulting culture broth filtrate (pH 7.6) was decolorized by passing through a column of Amberite XAD-2 (15 $l$), a synthetic adsorbent, the effluent (150 $l$) was further passed through a column of Dowex 1 × 2 (Cl type) (7 $l$), whereby the active ingredient was adsorbed on the resin. After washing with water and then eluted with a 0.05 M aqueous solution of sodium chloride. The first 10 l. portion was discarded and then the second 20 l. portion was passed through a column of active carbon (1 $l$) to make the active ingredient adsorbed on the carbon, and then eluted with water. The first 1 $l$ portion was discarded and the second 3 l. portion was then passed thrugh a column of DEAE Sephadex A-25 (Cl-type) (150 ml.) to have the active ingredient adsorbed thereon. After washing with water, and eluted with a 0.03 M aqueous solution of sodium chloride. The active fractions (400 ml.) were collected, and then subjected to a column of active carbon (40 ml.) so that the active ingredient was adsorbed by the active carbon and the active carbon was eluted with water. The active fractions were subjected to a thin-layer chromatography (n-butanol: acetic acid: water = 2:1:1, ninhydrin coloring) to combine those fractions which show a single and identical spot in the thin-layer chromatography. The combined fractions were then freeze-dried to give 430 mg of 7-(5-amino-5-carboxyvaleramido)-7-methoxy-3-hydroxymethyl-3-cephem-4-carboxylic acid (sodium salt) as white powder.

FIG. 1 shows infrared absorption spectrum of 7-(5-

Antibacterial activity of 7-(5-amino-5-carboxyvaleramido)-7-methoxy-3-hydroxymethyl-3-cephem-4-carboxylic acid (Na salt) (Paper disc method)

| Test microorganism | Diameter of inhibition zone (mm) | | |
|---|---|---|---|
| | 5 mg/ml | 2.5 mg/ml | 1.25 mg/ml |
| Bacillus stearothermophylus | 19.7 | 15.7 | 11.7 |
| Vibrio percolans ATCC8461 | 24.8 | 19.7 | 15.0 |
| Alcaligenes faecalis ATCC8750 | (22.2) | (20.0) | (16.7) |
| Proteus vulgaris | 19.0 | 16.7 | 11.7 |
| Micrococcus lysodeikticus | 19.7 | 17.0 | 11.4 |

The examples of this invention will be shown hereinbelow.

EXAMPLE 1

Spores of *Streptomyces chartreusis* SF-1623 strain (Deposit No. 2348 in Fermentation Research Institute of the Agency of Industrial Science and Technology, Inage, Chiba city, Japan) were inoculated to 500 ml. of a liquid medium of 1.0 % starch and 3.0 % soybean meal (pH 7.0), shaken culture was effected at 28°C. for 24 hours and then the cultured broth was inoculated to 20 l. of the same medium as above. Cultivation was effected for further 20 hours under aeration to produce a seed culture.

The seed culture thus made was inoculated to 200 l. of a liquid medium comprising 1.5 % glycerol, 2.0 % dextrin, 2.0 % soybean meal, 0.15 % calcium carbonate and 0.1 % L-cysteine hydrochloride (pH 7.0) and cultivation was carried out at 28°C. under aeration (using a 300 l. fermenter). After cultivation for 68 hours, a culture medium was filtered to yield 150 l. of a filtrate.

And, it was found that the substance SF-1623 (Japanese Patent Application No. 132594/1973) was not amino-5-carboxyvaleramido)-7-methoxy-3-hydroxymethyl-3-cephem-4-carboxylic acid (sodium salt) obtained by this example and FIG. 2 shows nuclear magnetic resonance spectrum of the same substance.

What is claimed is:

1. A process for the production of 7-(5-amino-5-carboxyvaleramido)-7-methoxy-3-hydroxy-methyl-3-cephem-4-carboxylic acid, which comprises cultivating *Streptomyces chartreusis* SF-1623 (ATCC 21999) or a mutant thereof in a culture medium under aerobic conditions whereby said carboxylic acid is produced, and recovering said carboxylic acid from the culture medium.

2. A process as claimed in claim 1, wherein *Streptomyces chartreusis* SF-1623 (ATCC 21999) is employed.

3. A process as claimed in claim 1 wherein said cultivation is effected at a temperature of about 22°to 35°C for 60–80 hours.

4. A process as claimed in claim 1 wherein said culture medium contains as a carbon source glucose, glycerol, starch, dextrin, sucrose, starch syrup, molasses, or soybean oil and as a nitrogen source soybean meal, wheat embryo, peptone, meat extract, dry yeast, corn steep liquor, fish meal, ammonium sulfate or sodium nitrate.

5. A process as claimed in claim 1 wherein said culture medium contains as an inorganic salt calcium carbonate, sodium chloride, potassium chloride or a phosphate salt.

6. A process as claimed in claim 1 wherein L-cystein is added to the said culture medium as a promoting substance.

* * * * *

UNITED STATES PATENT OFFICE
CERTIFICATE OF CORRECTION

PATENT NO. : 3,974,035
DATED : August 10, 1976
INVENTOR(S) : TAKASHI SHOMURA et al It is certified that error appears in the above—identified patent and that said Letters Patent are hereby corrected as shown below:

Column 3, lines 23-24: replace "to the strains to the strains" with --- to the strain ---.

Column 3, line 27: after "Vol. 19, pages", insert --- 391-512 ---.

Column 3, line 60: replace "chemical" with --- chemicals ---.

Column 5, line 22: replace "N, 9.85" with --- N, 9.88 ---.

Signed and Sealed this twelfth Day of July 1977

[SEAL]

Attest:

RUTH C. MASON
*Attesting Officer*

C. MARSHALL DANN
*Commissioner of Patents and Trademarks*